US008323507B2

(12) United States Patent
Rothmann et al.

(10) Patent No.: US 8,323,507 B2
(45) Date of Patent: Dec. 4, 2012

(54) DEVICE AND METHOD FOR THE ELIMINATION OF MAGNETIC PARTICLES FROM A LIQUID

(75) Inventors: Thomas Rothmann, Langenfeld (DE); Thomas Deutschmann, Wuppertal (DE); Christian Lenz, Düsseldorf (DE); Cordula (Leurs) Homberg, Neuss (DE)

(73) Assignee: Qiagen, GmbH, Hilden (DE)

( * ) Notice: Subject to any disclaimer, the term of this patent is extended or adjusted under 35 U.S.C. 154(b) by 715 days.

(21) Appl. No.: 11/990,520

(22) PCT Filed: Aug. 18, 2006

(86) PCT No.: PCT/EP2006/065451

§ 371 (c)(1), (2), (4) Date: Mar. 27, 2009

(87) PCT Pub. No.: WO2007/020294

PCT Pub. Date: Feb. 22, 2007

(65) Prior Publication Data

US 2009/0206039 A1 Aug. 20, 2009

(30) Foreign Application Priority Data

Aug. 18, 2005 (DE) ......................... 10 2005 039 175

(51) Int. Cl.
*B01D 35/06* (2006.01)
*G01N 33/553* (2006.01)

(52) U.S. Cl. ........ 210/695; 210/222; 209/217; 209/226; 209/227; 422/553; 436/526

(58) Field of Classification Search .................. 210/222, 210/223, 695; 209/217–218, 225–227; 422/553; 436/526

See application file for complete search history.

(56) References Cited

U.S. PATENT DOCUMENTS

| | | | | | |
|---|---|---|---|---|---|
| 9,610 | A * | 3/1853 | Gardiner, Jr. | ................. | 209/219 |
| 2,088,364 | A * | 7/1937 | Ellis et al. | ...................... | 209/214 |
| 2,604,207 | A * | 7/1952 | Scott | ............................ | 209/218 |
| 2,661,092 | A | 12/1953 | Injeski | | |
| 2,826,302 | A * | 3/1958 | Scott | ............................ | 209/218 |
| 3,168,464 | A | 2/1965 | Ferris et al. | | |
| 3,295,678 | A | 1/1967 | Genier | | |
| 4,080,760 | A * | 3/1978 | Leliaert | .......................... | 451/88 |
| 5,536,475 | A | 7/1996 | Moubayed | | |
| 5,942,161 | A * | 8/1999 | Pate | ............................... | 261/91 |
| 6,432,630 | B1 * | 8/2002 | Blankenstein | .................... | 435/4 |
| 2002/0137226 | A1 * | 9/2002 | Tanaami | ...................... | 436/149 |
| 2005/0250221 | A1 | 11/2005 | Horita | | |

FOREIGN PATENT DOCUMENTS

| | | | |
|---|---|---|---|
| EP | 0 133 869 | A2 | 3/1985 |
| EP | 0 905 520 | A | 3/1999 |
| JP | 2005-300396 | | 10/2005 |
| WO | WO 2005/059085 | A1 * | 6/2005 |

* cited by examiner

*Primary Examiner* — Tony G Soohoo
*Assistant Examiner* — David C Mellon
(74) *Attorney, Agent, or Firm* — Fanelli Haag & Kilger PLLC

(57) ABSTRACT

Device for the separation of magnetic particles from a liquid, comprising a first vessel (10), a second vessel (20), a connecting surface (11, 21, 30; 200) that runs from the interior of the first vessel (10) to the interior of the second vessel (20), at least one magnet (40) for the provision of a magnetic field, and a guide element (50) by means of which the magnetic field can be guided along one side of the connecting surface (11, 21, 30; 200).

32 Claims, 13 Drawing Sheets

DEVICE AND METHOD FOR THE ELIMINATION OF MAGNETIC PARTICLES FROM A LIQUID

RELATED APPLICATIONS

Figure 1A:
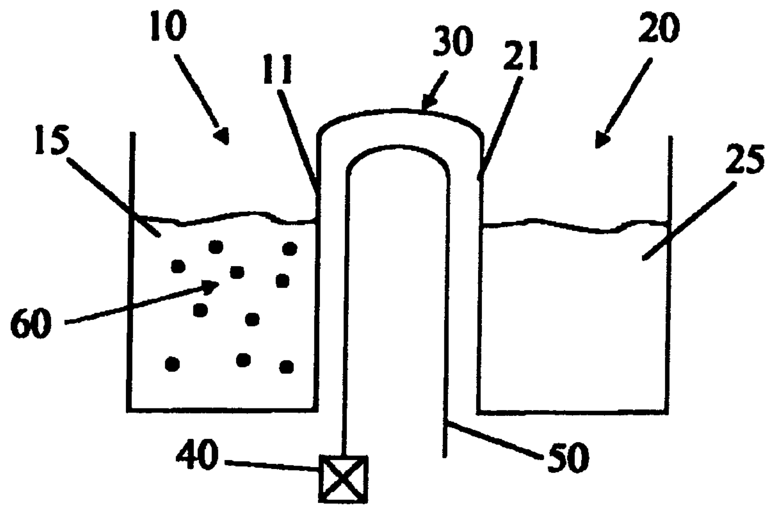

This application is the U.S. National Phase under 35 U.S.C. §371 of International Application No. PCT/EP2006/065451, filed on Aug. 18, 2006, which in turn claims the benefit of German Application No. 10 2005 039 175.3, filed on Aug. 18, 2005 the disclosures of which applications are incorporated by reference herein.

The present invention relates to a device for the separation of magnetic particles from a liquid and a method for the separation of magnetic particles from a liquid. The device and the method are suitable, for example, for applications in biochemistry, molecular genetics, microbiology, medical diagnostics or forensic medicine.

Methods based on the magnetic separation of specifically and/or non-specifically binding magnetic particles are becoming increasingly important in the area of sample preparation for diagnostic or analytical investigations, in particular for the isolation of nucleic acids. This applies in particular for automated methods since in this way a large number of samples can be prepared within a short period of time and work-intensive centrifugation steps can be dispensed with. By these means the requirements for efficient screening with high sample throughput are met. This is of considerable importance, since purely manual handling of a very large number of samples is unmanageable in practice. Another important application of magnetic particles are pharmaceutical screening methods for the identification of potential active drug ingredients.

The fundamental principle of magnetic separation of substances from complex mixtures is based on magnetic particles being equipped with specific binding properties for the target substances to be separated by, for example, chemical treatment of their surfaces. The size of such magnetic particles generally lies in the range of ca. 0.05 to 500 μm, so that they provide a large surface for the binding reaction. Moreover, the magnetic particles can have a density that is similar to the density of the liquid in which they are suspended. In this case sedimentation of the magnetic particles can well last several hours.

In known separation methods the magnetic particles are immobilised in one position by application of magnetic forces or a magnetic field, for example by means of a permanent magnet. The collection of magnetic particles is also termed a pellet. The liquid supernatant is subsequently removed by, for example, siphoning off or decanting and is rejected. Since the magnetic particles are immobilised by the magnetic forces it is essentially prevented that the magnetic particles are separated together with the supernatant.

Typically the immobilised magnetic particles are subsequently re-suspended. For this purpose an elution liquid or an elution buffer is used that is suited to breaking down the binding between the target substance and the magnetic particles so that the target substance molecules are released from the magnetic particles. The target substance molecules can then be separated with the elution liquid, while the magnetic particles are immobilised by the action of the magnetic field. One or more wash steps can be carried out before the elution step.

Different devices for carrying out such separation methods for magnetic particles have been described. Thus, US 2001/0022948 describes a device with which a magnetic rod is immersed in a first reaction vessel that contains the magnetic particles suspended in the liquid. There the magnetic rod attracts the magnetic particles so that the magnetic particles adhere to the rod. The magnetic rod together with the adhering magnetic particles are withdrawn from the first reaction vessel and introduced into a second reaction vessel. There the magnetic force of the rod is reduced or switched off so that the magnetic particles are released from the rod and are suspended in the liquid contained in the second reaction vessel. Similar methods are also known from U.S. Pat. No. 6,065,605 and WO 2005/005049.

In contrast, a device is known form EP 0 965 842 with which the magnetic particles and the liquid in which they are suspended are drawn into a pipette. The pipette tip has a special separation region to which a magnetic field can be applied with a magnet. In this way the magnetic particles are immobilised as pellet on the inside of the pipette tip. The pipette liquid is next removed from the pipette tip by the pipetting function. The magnetic field in the separation region can then be withdrawn through which the magnetic particles immobilised in the pellet can be released once more. A similar method and a similar device are described in U.S. Pat. No. 6,187,270.

EP 0 905 520 describes another principle for the separation of magnetic particles. Here the magnetic particles remain in the same reaction vessel while the liquid in this vessel is exchanged. In this way the pellets can be immobilised at a desired height on the side walls of the reaction vessel for adaptation to the respective process step. This is carried out by the provision of magnets that are mounted on different arms of a pivoted carrier at correspondingly different distances from the axis of rotation. By rotating the carrier a particular arm—and thus a particular magnet—can be brought in each case into the proximity of the side wall of the reaction vessel. The magnetic particles are then immobilised as a pellet at this position.

The conventional devices and methods named all have the common characteristic that they are all constructed as so-called open systems, since according to their respective mode of operation magnetic rods or pipettes must be inserted into the reaction vessel once or several times. In that way the risk of cross contamination of other reaction vessels by aerosol or droplet formation exists with these conventional devices and methods. As a result experimental results can be adulterated or be even unusable.

It is therefore the problem of the present invention to overcome at least in part the problems of the state of the art described above.

This problem is solved by a device as disclosed herein and a method as disclosed herein. Further details, advantages and aspects of the present invention are revealed by the description and the attached drawings.

According to one embodiment of the present invention a device for the separation of magnetic particles from a liquid is provided, comprising a first vessel, a second vessel, a connecting surface that connects the inside of the first vessel with the inside of the second vessel, at least one magnet for the provision of a magnetic field, and a guide element by means of which the magnetic field can be directed along one side of the connecting surface.

With such a device magnetic particles that are suspended in the liquid located in the first vessel can be separated from this liquid without a magnetic rod or a pipette tip having to be introduced into the first vessel. Moreover, the magnetic particles can be formed into a pellet by the magnetic field, and this pellet can be transported into the second vessel along the connecting surface by the guide element fitted externally to the vessel. In this way the risk of cross-contamination, for example, by liquid dropping off the magnetic rod or pipette tip is considerably reduced or even eliminated. Moreover, the device can be provided as a closed system and thus the risk of cross-contamination further reduced.

Depending on the respective application the length of the connecting surface can be so selected that any influence upon the particle, for example drying of the particle, can be either supported or reduced.

According to another embodiment of the present invention the connecting surface can be formed by a first side wall of the first vessel, a second side wall of the second vessel and a bridging section connecting the first and the second side wall.

In this way no separate connecting surface need be provided. In particular, the first and the second vessel can be formed as wells of a microtiter plate. As an alternative to this embodiment the first and the second vessel and the connecting surface can be provided as separate elements. Here, for example, the connecting surface can be constructed as a bridge or tube.

According to another embodiment of the present invention a permanent magnet is used. In this way the magnetic field can be provided cost-effectively. The guide element would then be so constructed that the magnet would be movable mechanically along the connecting surface. An alternative to this could be that at least one of the magnets is also constructed as an electromagnet. In this case too the electromagnet can be directed mechanically along the connecting surface. Furthermore, several electromagnets can also be mounted behind one another, for example on the underside of the connecting surface. The guide element would then control the electromagnets in a timed sequence and activate and deactivate them so that the magnetic field produced by the electromagnets would migrate along the connecting surface from the first to the second vessel.

According to a further embodiment of the present invention the guide element is so constructed that the at least one magnet is moveable at a prescribed fixed distance from the connecting surface. In particular, the prescribed fixed distance can be zero so that the magnet is in contact with the connecting surface as it moves along it.

In this way it can be ensured that on the way from the first vessel to the second vessel an essentially constant magnetic field is applied to the magnetic particles shaped into a pellet. In this way it is possible effectively to prevent magnetic particles separating from the pellet as a result of a weakening of the magnetic force.

According to another embodiment of the present invention at least one heating and/or cooling element, for example a heating wire or Peltier element, is provided on the connecting surface. By using heating and/or cooling elements the magnetic particles can be held at a prescribed temperature on their way.

According to another embodiment of the present invention the connecting surface is shaped as an arc along the path of the at least one magnet. The guide element is then typically so shaped that the minimum one magnet is movable along an arcuate pathway, whereby the radius of the arcuate pathway is smaller or the same as the radius of the arc from which the connecting surface is formed.

In this way a particularly simple form of control can be implemented in which the magnet is namely moved on a circular orbit or along an arc with constant radius. The guide element can be mounted on a shaft, through which the drive and the control of the guide element can be configured particularly simply. This also allows simple automation of the operation procedures.

According to a further example of the present invention at least one third vessel is further provided, which is connected with the first or second vessel by means of a second connecting surface as well as a second guide element to which at least one further magnet is mounted. In this way the first or second vessel together with the third vessel, the second connecting surface, the second guide element and the further magnets form a further device for the separation of magnetic particles as described above.

Thus, after the first separation of the magnetic particles from the liquid in the first vessel one or, if several vessels and guide elements are interconnected, several washing steps can be carried out before the magnetic particles are transported to an elution solution.

According to a still further embodiment of the present invention at least one of the vessels has a function element, in particular an outlet and/or filter. Subsequent analysis steps, for example, may be prepared with this function element, such as a PCR step (polymerase chain reaction). The outlet preferably has attachment possibilities with the help of which reaction stubs, for example, may be attached to the outlet.

According to a further embodiment of the present invention the vessels can be constructed as a cartridge. This allows a compact construction, in this way a so-called lab-on-a-chip in particular can be realised. In such a lab-on-a-chip all devices necessary for carrying out an investigation can be integrated on a chip or cartridge.

According to another aspect of the present invention a method for the separation of magnetic particles from a liquid is provided that comprises the following steps:

(a) provision of a first vessel, a second vessel, a connecting surface which connects the interior of the first vessel with the interior of the second vessel, and a guide element for directing a magnetic field;

(b) provision of a suspension of magnetic particles in a first liquid in the first vessel;

(c) provision of at least one magnetic field by means of the guide element at a region of the connecting surface located within the interior of the first vessel so that a pellet is formed from the magnetic particles at this region;

(d) directing the at least one magnetic field along one side of the connecting surface with the guide element to a region of the connecting surface arranged within the interior of the second vessel so that the pellet of magnetic particles is transported along the connecting surface into a region located in the interior of the second vessel;

(e) withdrawal of the at least one magnetic field by means of the guide element from the region of the connecting surface located within the interior of the second vessel so that the magnetic particles forming the pellet are once more released.

Such a method can be carried out simply in, for example, a device according to one embodiment of the present invention in automated form. In such a separation method the risk of cross-infection is considerably reduced in comparison to the state of the art since no insertion of a magnetic rod or pipette tip into the vessel is necessary. Therefore the risk of liquid dropping from the magnetic rod or the pipette tip is excluded.

In the following the details of the invention are illustrated on the basis of different embodiments with reference to the attached drawings. Shown therein:

FIGS. 1A to 1E a schematic representation of a device and a method according to one embodiment of the present invention.

FIGS. 2A to 2E a schematic representation of a device and a method according to a further embodiment of the present invention.

Figure 3A:
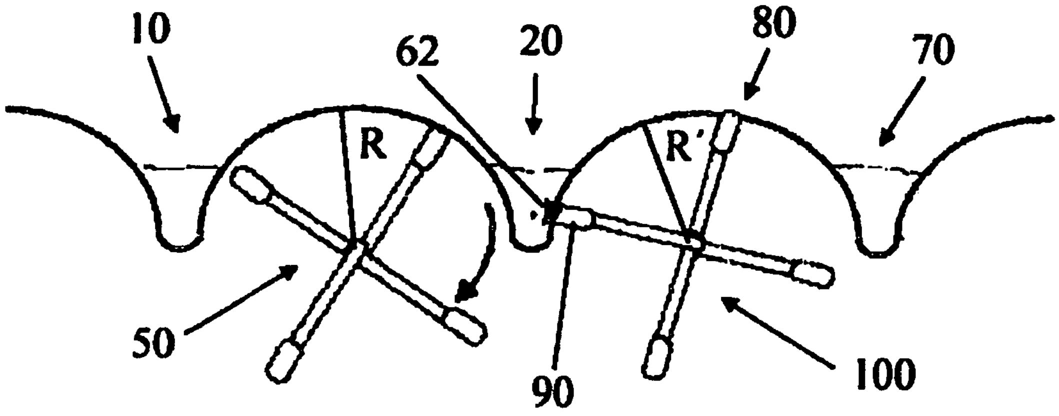
Figure 3B:
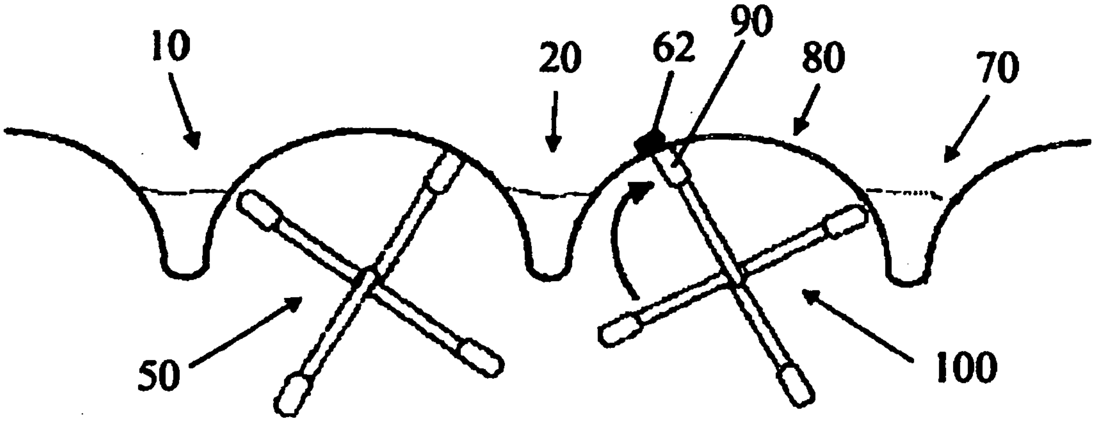
Figure 3C:
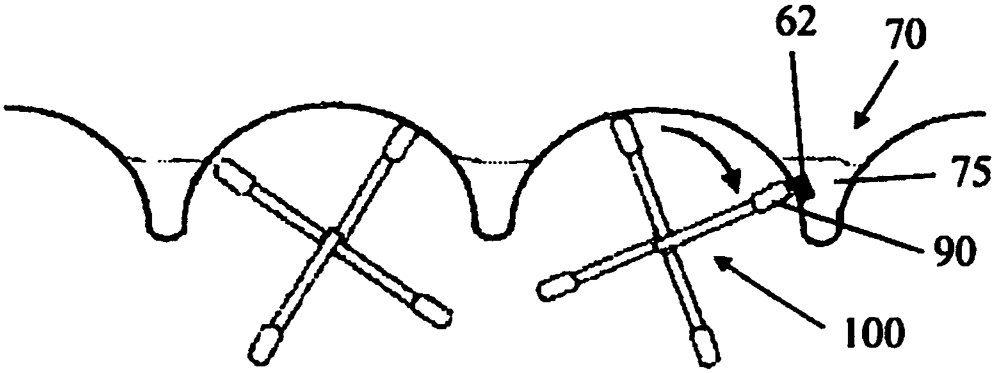

FIGS. 3A to 3C a schematic representation of a device and a method according to a still further embodiment of the present invention.

Figure 4A:
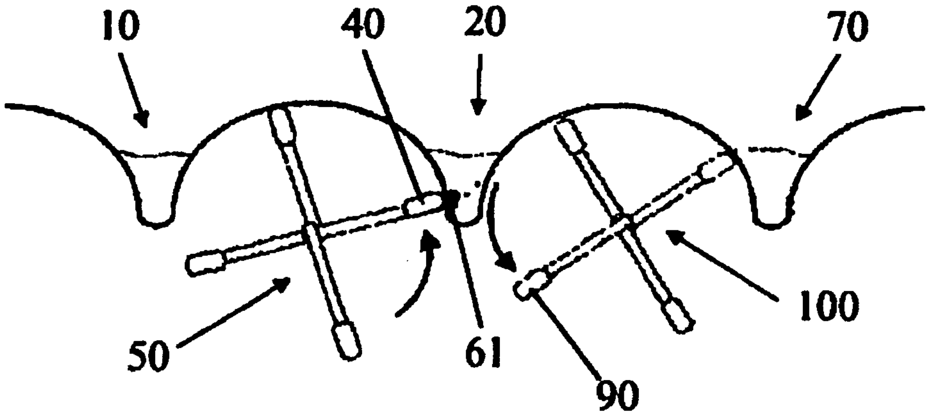
Figure 4B:
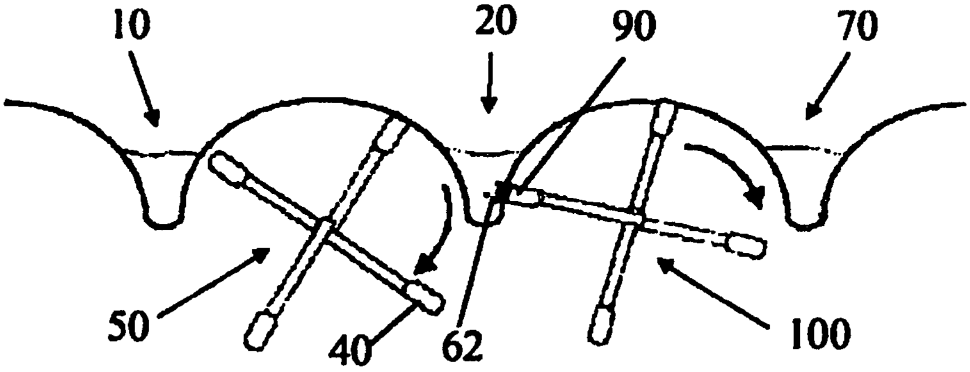

FIGS. 4A to 4B a schematic representation of a wash step according to one embodiment of the present invention.

Figure 5:
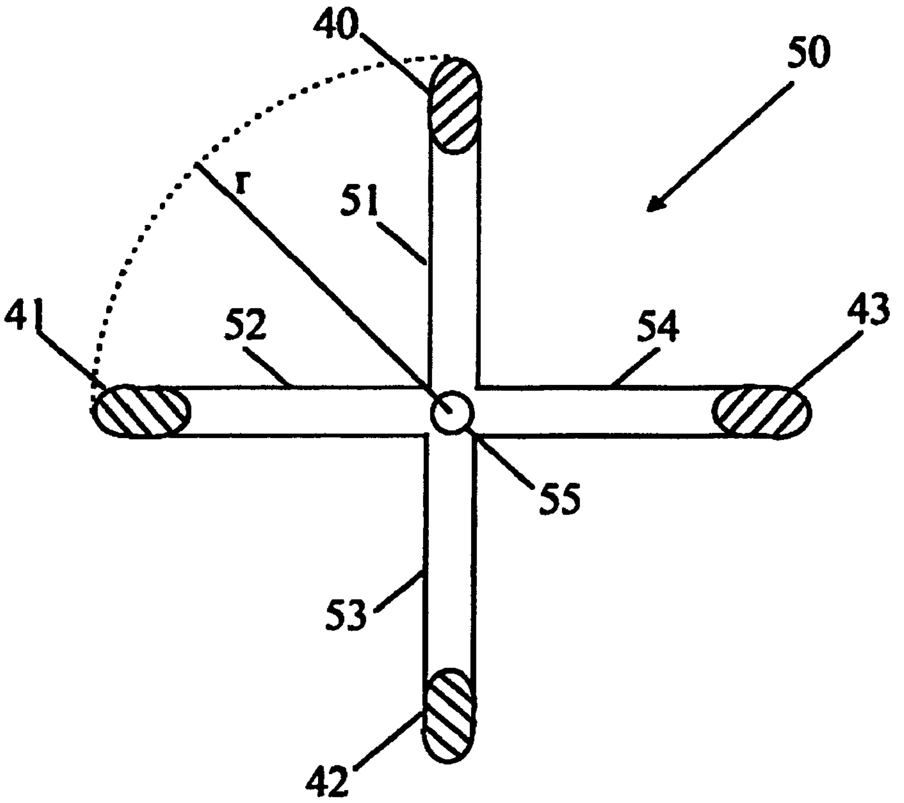

FIG. 5 a guide element according to one embodiment of the present invention.

Figure 6:
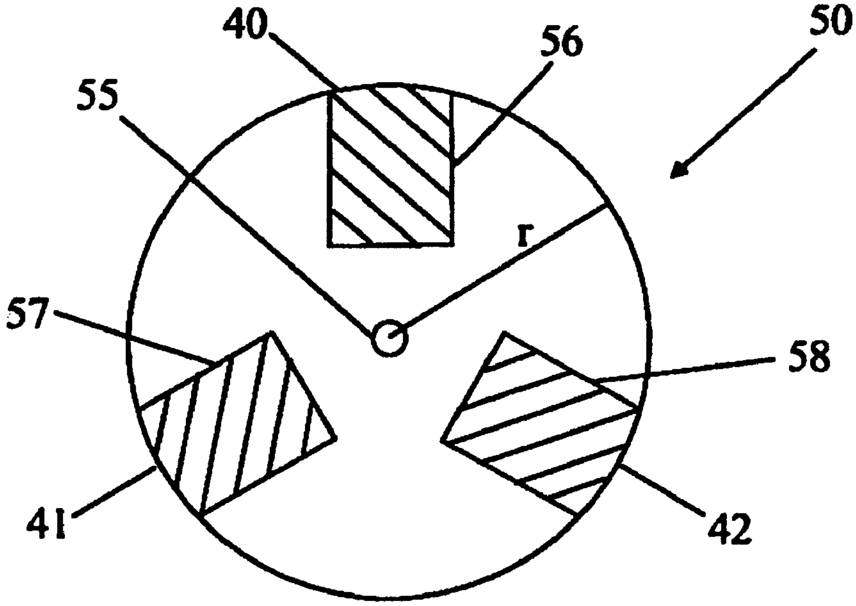

FIG. 6 a guide element according to another embodiment of the present invention.

Figure 7:
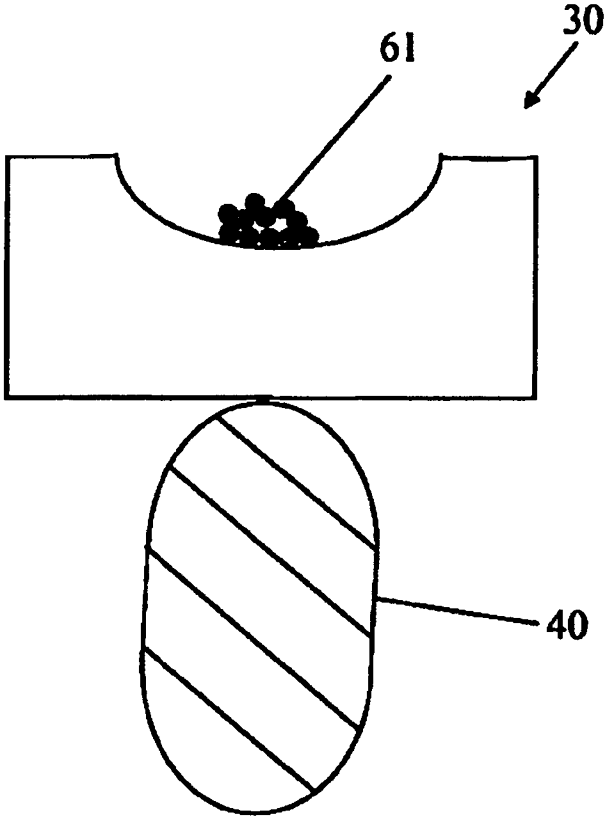

FIG. 7 a cross-sectional view of a bridging section according to one embodiment of the present invention.

Figure 8:
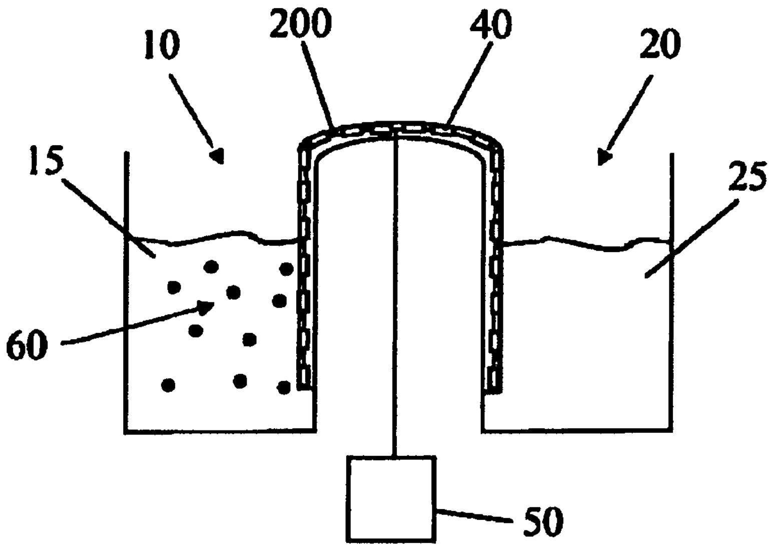

FIG. 8 another embodiment of the present invention.

Figure 9:
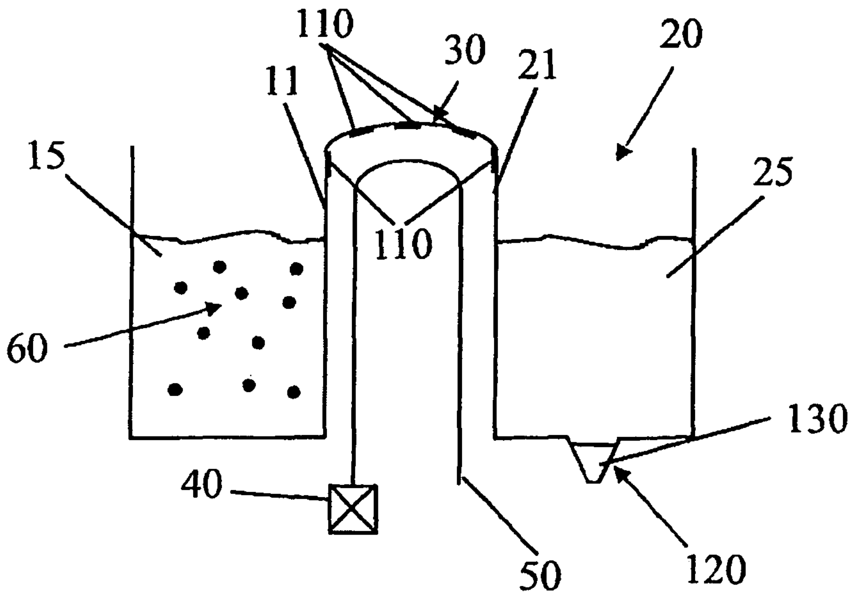

FIG. 9 a further embodiment of the present invention.

Figure 10:
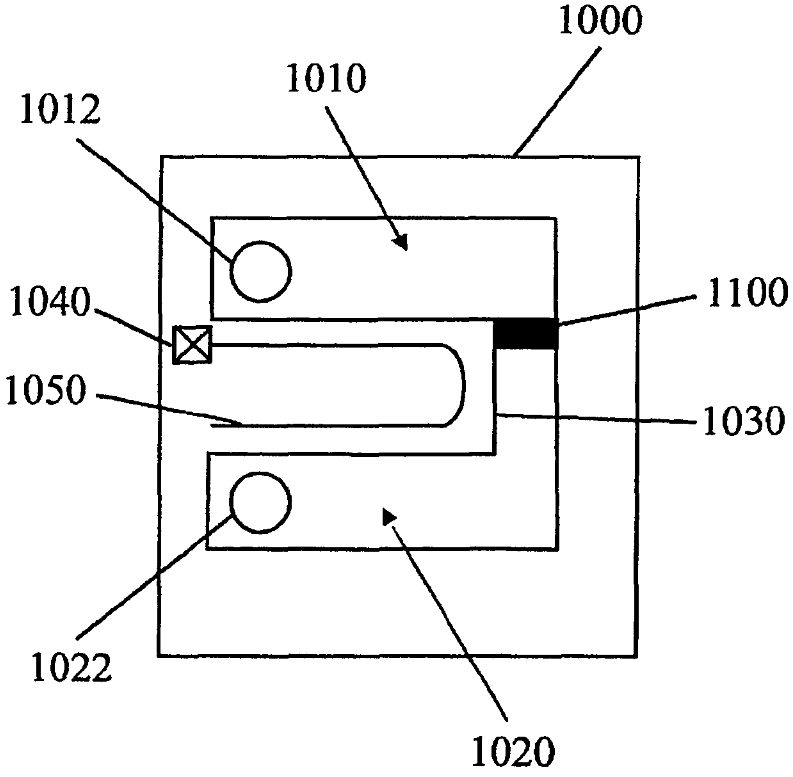

FIG. 10 a schematic representation of a further embodiment of the present invention in which the invention is realised in a cartridge.

FIGS. 11A to 11F a schematic representation how a method according to the invention is realised in the embodiment shown in FIG. 10.

Figure 12:
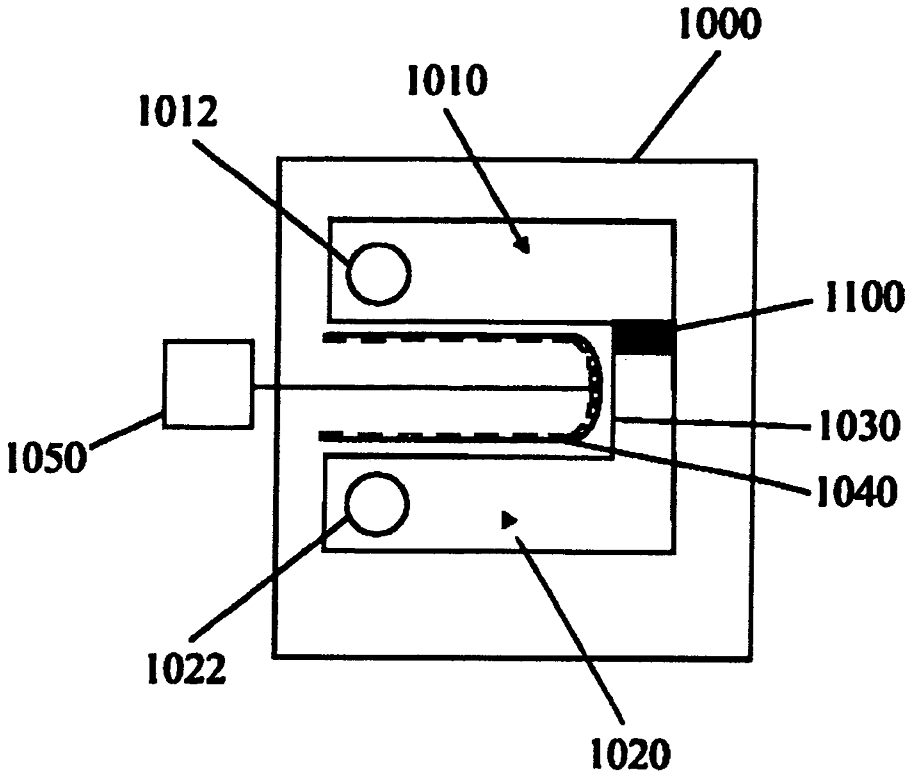

FIG. 12 a schematic representation of a variant of the embodiment of the present invention shown in FIG. 10.

Figure 13:
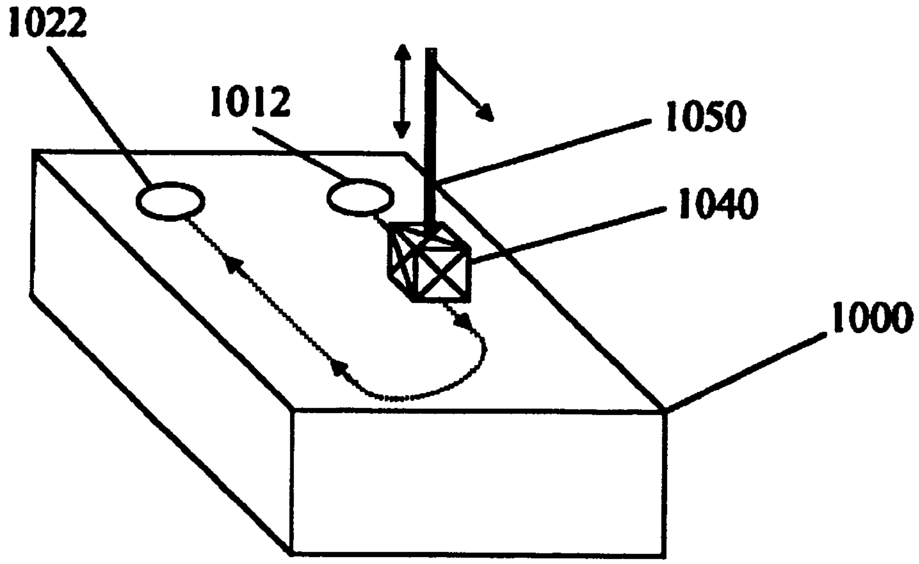

FIG. 13 a schematic representation of another variant of the embodiment of the present invention shown in FIG. 10.

Figure 14:
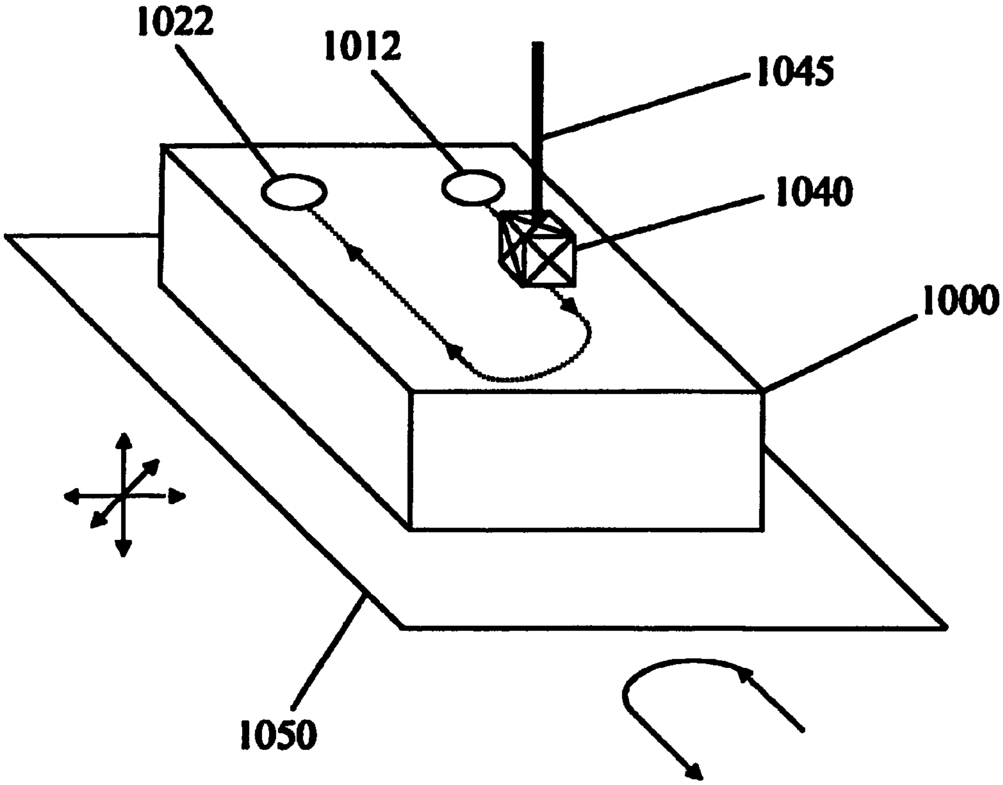

FIG. 14 a schematic representation of a further variant of the embodiment of the present invention shown in FIG. 10.

Figure 15:
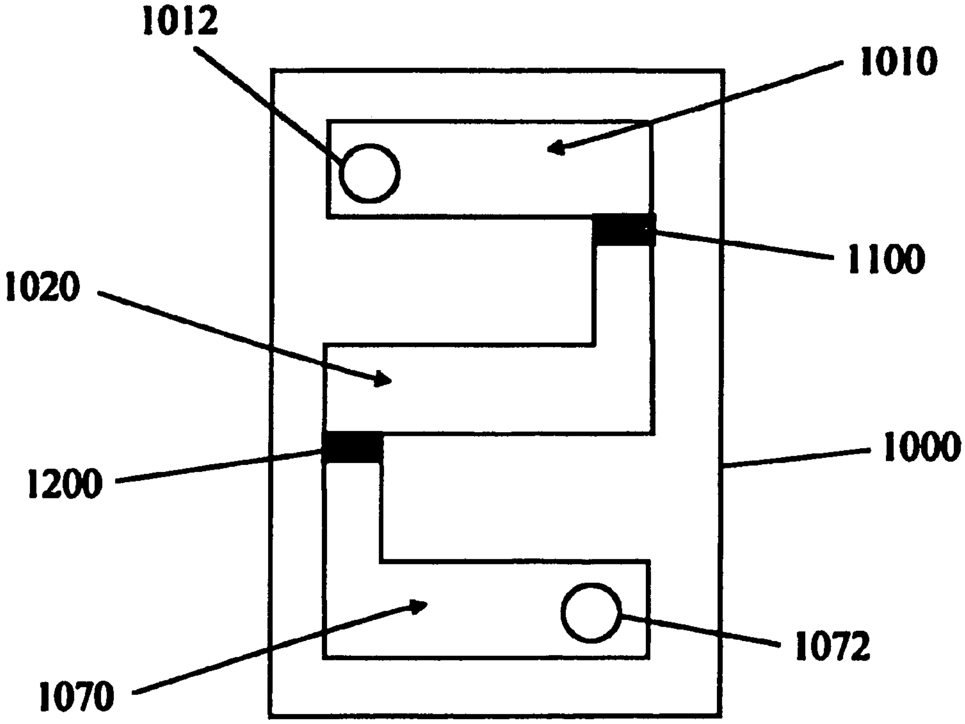

FIG. 15 a schematic representation of a further development of the embodiment of the present invention shown in FIG. 10.

In the following description of different embodiments of the present invention functionally identical features of the different embodiments are provided with the same reference symbol.

FIG. 1A shows a schematic representation of a device according to one embodiment of the present invention. In a first vessel 10 is located a liquid 15 in which magnetic particles 60 are suspended. In addition a second vessel 20 is shown, in which is located a second liquid 25, e.g. a wash solution or an elution solution. The first vessel 10 has a first side wall 11 that is connected to a second side wall 21 of the second vessel 20 by a bridging section 30. In this embodiment the first side wall 11, the second wall 21 and the bridging section 30 form a connecting surface that runs from the interior of the first vessel 10 to the interior of the second vessel 20. However, such a connecting surface could also be provided as a bridge in the form of an inverted U separately constructed from the first and the second vessel, which is inserted into the first and the second vessel. Furthermore, the connecting surface could also be formed by a tube, one end of which is arranged in the interior of the first vessel and the other end of which is arranged in the interior of the second vessel.

In addition a magnet 40 is provided that can be in the form of a Neodymium permanent magnet or electromagnet. The magnet 40 is attached to a guide element 50. The guide element 50 is so arranged that it can direct the magnet 40, and thus the magnetic field produced by, it along the connecting surface from the interior of the first vessel 10 into the interior of the second vessel 20. In the present embodiment this means that the guide element 50 can direct the magnet 40 along the first side wall 11 and along the underside of the bridging section 30 to the second side wall 21. A cylindrical roller or a rotary arm can be used as guide element 50, as will be explained further later in this application. It is also possible that the magnet 40 can be arranged, for example, on a flexible belt that is directed along the side walls 11 and 21 and the underside of the bridging section 30. The guide element 50 is so constructed that it holds the magnet 40 at a prescribed fixed distance form the connecting surface, i.e. the side walls 11, 21 and the underside of the bridging section 30. The prescribed fixed distance is so selected that the magnetic attraction which the magnet 40 exerts on the suspended magnetic particles 60 when it is brought up to the side wall 11 is sufficient for the suspended particles to be immobilised as a pellet 61 on the side wall 11. (see FIG. 1B) In particular, the distance between the magnet 40 and the side walls 11, 21 and the underside of the bridging section 30 can be zero. In this case the magnet 40 is in contact with the side walls 11, 21 and the underside of the bridging section 30 as it is directed past.

According to a further embodiment of the present invention the connecting surface can be constructed in the form of a groove. FIG. 7 shows a cross-section of the bridging section 30 which is constructed in the form of a groove-like recess on its upper side between the first vessel 10 and the second vessel 20. In this way it is possible to prevent any of the first liquid 15 which may possibly be adhering to the pellet 61 detaching itself in the upper part of the bridging section 30, leading to cross-contamination. Should liquid actually be detached during the movement of the pellet 61 for the first to the second vessel this will be lead back into the first or the second vessel in the groove.

Figure 1B:
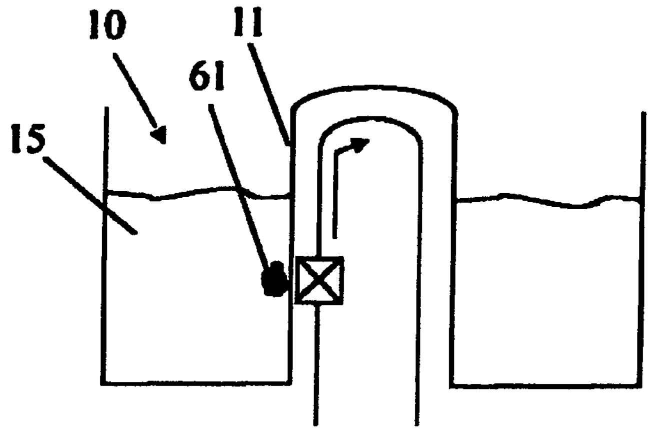
Figure 1C:
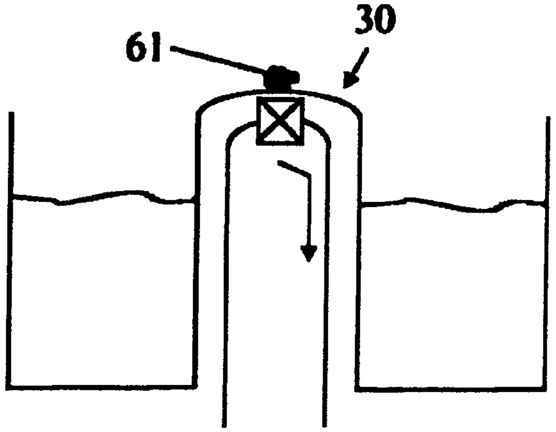
Figure 1D:
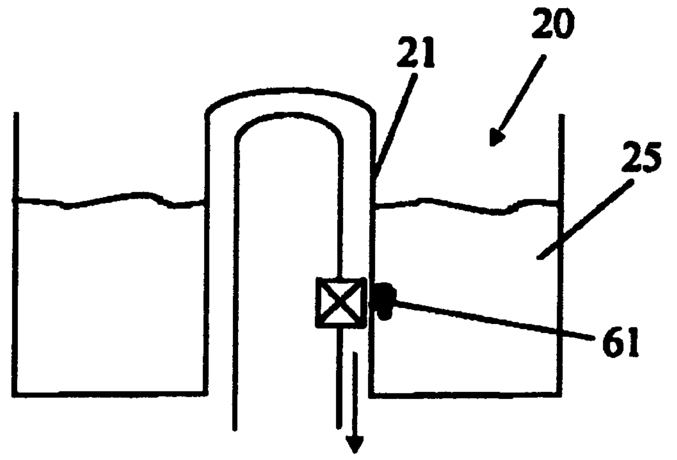
Figure 1E:
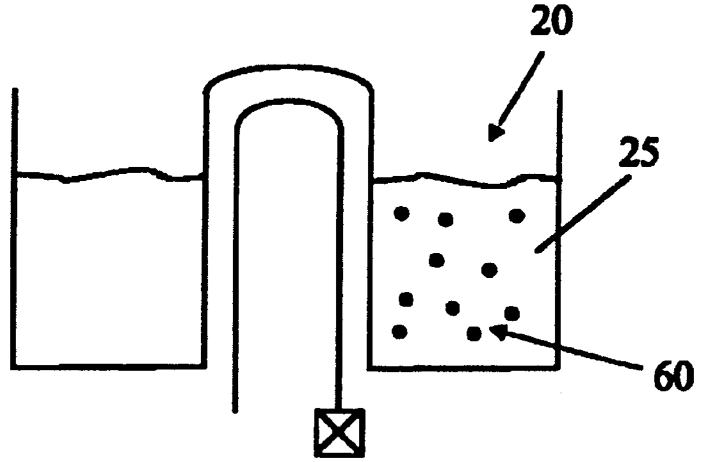

In the following, a method according to one of the embodiments of the present invention is described on the basis of the FIGS. 1A to 1E. The initial state is shown in 1A, in which the magnetic particles 60 are suspended in the liquid 15 in the first vessel 10. The magnet 40 is arranged externally to the region of the side wall 11 of the first vessel 10. As FIG. 1B shows, the magnet 40 is brought up to the side wall 11 of the first vessel 10 by the guide element 50. There it attracts the magnetic particles 60, which are immobilised on the side wall 11 as pellet 61. Next the magnet 40 is directed by the guide element 50 along the side wall 11 over the bridging section 30 to the side wall 21 of the second vessel 20, see FIGS. 1C and 1D. The magnetic particles formed into the pellet 61 by the magnetic force follow the movement of the magnet 40 as a result of the magnetic attraction. In this way the pellet 61 is transported along the connecting surface, i.e. along the inner side 11 over the upper side of the bridging section 30 to the inner wall 21 of the second vessel 20. A shown in FIG. 1E, the magnet 40 is finally removed from the side wall 21 of the second vessel 20 so that the magnetic particles forming the pellet 61 are again released. The magnetic particles 60 are re-suspended in the liquid 25 of the second vessel 20. e.g. in a wash or elution solution.

A further embodiment of the present invention is now described on the basis of FIGS. 2A to 2E. Here too a first and second vessel 10, 20 are provided, which are connected to one another by the connecting surface 11, 21, 30. The connecting surface is again formed by a side wall 11, a second wall 21 and a bridging section 30. Here the connecting surface, i.e. here the first side wall 11, the second wall 21 and the bridging section 30, is so shaped as to form an arc with a radius R. Typically the side walls 11, 21 and the bridging section 30 are constructed in one piece as connecting surface. As already explained above, the first and second vessel as well as the connecting surface can also be provided as separable elements. The guide element 50 is constructed as a four-arm spider, as shown enlarged in FIG. 5.

In FIG. 5 the guide element has four rotary arms 51, 52, 53, 54 that are mounted rotatably on a shaft 55. Magnets 40, 41, 42, 43 are arranged on each of the rotary arms 51, 52, 53, 54 distant from the shaft 55. The total length r of the rotary arms 51, 52, 53, 54 including the magnets 40, 41, 42, 43 is smaller than or equal to the radius R of the arc so that the magnets 40, 41, 42, 43 can be directed along the side walls 11, 21 and the bridging section 30 at a distance of R−r. If the total length r is the same as the arc radius R the magnets 40, 41, 42, 43 are in contact with the side walls 11, 21 and the bridging section 30 when they pass by these. It is beneficial in this case, when the surfaces of the magnets 40, 41, 42, 43 which are in contact with the side walls 11, 21 and the bridging section 30 are curved, whereby the curvature radius is smaller than the arc radius R.

According to FIG. 5 the four rotary arms are integrated, however, they can be constructed as individual rotary arms and mounted singly on the shaft 55. In addition, the number of four rotary arms is merely exemplary, for, depending on application, fewer or more rotary arms can be provided. In particular it is possible to provide simply a single rotary arm. Furthermore, the four pivot arms in FIG. 5 are offset at 90° to one another, i.e. equally distributed over the circumference 2π r swept by the spider. However, depending on the application the two or more pivot arms can also be arranged offset at any suitable angular distance relative to one another.

Figure 2A:
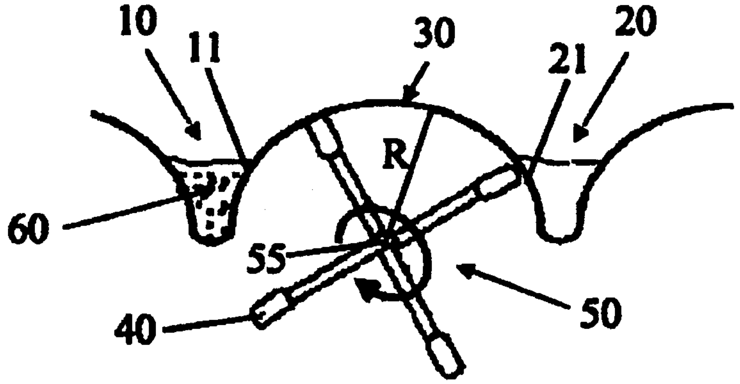

Another embodiment of a guide element 50 that can be used in the device shown in FIG. 2A is shown in FIG. 6. Here the guide element 50 is constructed in the form of a cylindrical roller or wheel with a radius r that is smaller or equal to the arc radius R. According to FIG. 6 the three magnets 40, 41, 42 are offset in each case by 120° in the housings 56, 57, 58. However, it would also be feasible for the magnets to be arranged on the surface of the cylindrical guide element, whereby the radius r together with the thickness of the magnets must then be smaller or equal to the arc radius R. Here too the number and relative position of the magnets can naturally vary according to the demands of the respective application. In particular, it is feasible that the magnets 40, 41, 42 may be removed from the housings 56, 57, 58 so that the number of magnets can vary from one up to the number of housings.

Figure 2B:
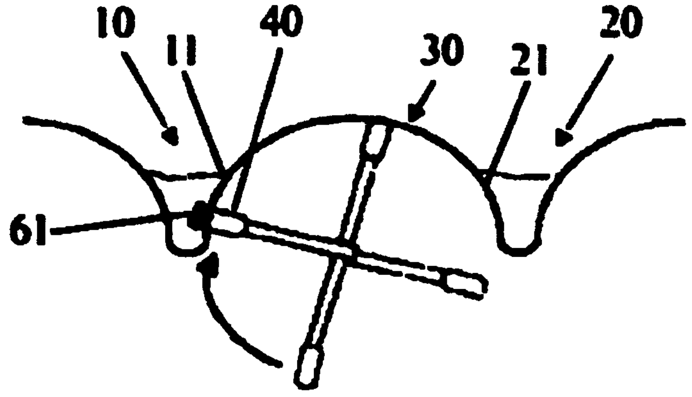
Figure 2C:
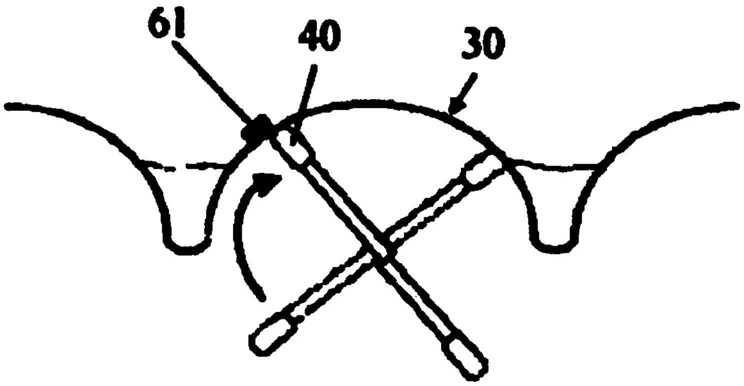
Figure 2D:
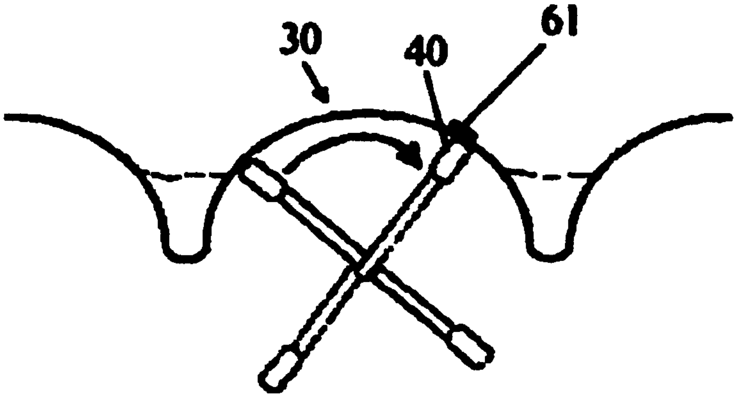
Figure 2E:
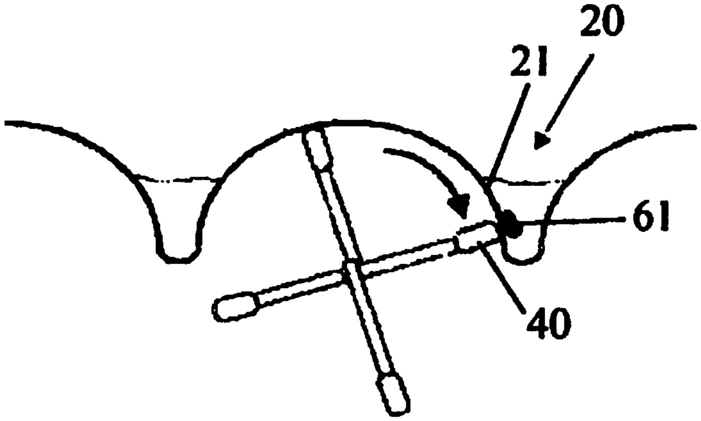

The functional mode of the embodiment shown in FIG. 2A is reproduced in FIGS. 2A to 2E. Initially the magnet 40 is moved up to the side wall 11 of the first vessel 10 where the magnetic particles then form a pellet 61 (FIG. 2B). The magnet 40 is then directed along the arc when it is followed by the pellet 61 (FIGS. 2C and 2D). The pellet 61 is then transported into the second vessel 20 (FIG. 2E) and finally the magnet 40 is removed from the second side wall 21 so that the magnetic particles are re-suspended in the liquid contained in the second vessel (not shown). In this way the pellet is transported from the interior of the first vessel along the connecting surface to the interior of the second vessel.

A further embodiment of the present invention is shown in FIGS. 3A to FIG. 3C. Here a third vessel 70 is additionally provided which is connected to the second vessel 20 through a second bridging section 80. In this way the side walls of the second and third vessels and the second bridging section form a second connecting surface that is formed as an arc with radius R'. The arc radius R' is typically equal to the arc radius R between the first and the second vessel, but depending on the nature of the application can also be selected to be different from R. Furthermore, a second guide element 100 with at least one further magnet 90 is situated between the respective opposite side walls of the second and the third vessels. With the help of the magnet 90 and the second guide element 100, the magnetic particles transported from vessel 10 to vessel 20 and re-suspended there can be combined into a second pellet 62 at the side wall of the second vessel. In the same way as between the first and the second vessel, the pellet 62 can be transferred into the third vessel 70 from the second vessel over the second connecting surface. If the magnet 90 is withdrawn from the side wall of the third vessel 70 the magnetic particles can be re-suspended in the liquid 75 situated in the third vessel 70. For example, with this device a wash solution can be provided in the second vessel and an elution solution in the third vessel. In this case the eluted magnetic particles can be transported back once more to the second vessel by reverse rotation of the second guide element and then disposed of. Furthermore, further vessels with connecting surfaces and guide elements with magnets mounted between them can naturally be provided, whereby liquids required for a precise method can be provided in the respective vessels.

According to a further embodiment of the present invention the device shown in FIG. 3A can also be used for carrying out a wash process as follows. Firstly the first pellet 61 from the first vessel 10 is transferred into the second vessel 20 filled with wash solution. There the magnet 40 is removed from the side wall of the second vessel along a first direction of rotation so that the magnetic particles are re-suspended in the wash solution. The magnet 90 mounted on the second guide element 100 is brought up to the opposite side wall of the second vessel along a first direction of rotation so that the magnetic particles form a second pellet 62 there. Thereby the first direction of rotation of the first guide element 50 is opposed to the first direction of rotation of the second guide element 100. Next the magnet 90 is removed from the side wall of the second vessel along a second direction of rotation. Now the second pellet 62 breaks down and the magnetic particles are re-suspended in the wash solution. Then the magnet 40 mounted on the first guide element 50 is brought up to the opposite side wall of the second vessel along a second direction of rotation so that the magnetic particles reform the first pellet 61. Thereby the second direction of rotation of the first guide element 50 is opposed to the second direction of rotation of the second guide element 100. In this way the first and the second direction of rotation of the first guide element can be the same or opposed. Also the first and the second direction of rotation of the second guide element can the same or opposed. The procedure can be repeated as often as necessary until the wash procedure is successfully concluded.

In the following a further embodiment of the present invention is described on the basis of FIG. 8. Here the first vessel 10 and the second vessel 20 are provided as separate vessels. A connecting surface 200 is shaped as a bridge, in the form of an inverted U, whereby the first end of the connecting surface 200 is located in the first vessel 10 and a second end of the connecting surface 200 is located in the second vessel 20. Typically the connecting surface 200 is grooved on its upper surface. Several electromagnets 40 are integrated into the connecting surface 200, mounted in a sequence one after the other from the first vessel 10 to the second vessel 20. For example, the connecting surface 200 could be constructed of a injection moulding in which the electromagnets are embedded. The electromagnets may be controlled individually by a single guide element 50, i.e. in each case activated and deactivated.

In this embodiment separation of the magnetic particles takes place as follows: firstly all electromagnets 40 under the connecting surface 200 are deactivated and the connecting surface is arranged in the first and second vessel as shown. The guide element 50 then activates the lower electromagnet(s) at the first end of the connecting surface that is situated in the first vessel. As a result of the magnetic attraction a pellet of magnetic particles is formed. The neighbouring electromagnets that are arranged along the connecting surface 200 closer to the end situated in the second vessel are activated one after the other in a time sequence and the electromagnets are deactivated again from the first end of the connecting surface. In this way the magnetic field migrates from the first end of the connecting surface to the second end of the connecting surface, and the pellet completes this movement as a result of the magnetic attraction. Once the pellet has finally reached the interior of the second vessel the electromagnets are deactivated and the magnetic particles forming the pellet are re-suspended in a liquid 25 in the second vessel 20. In this way separation of the magnetic particles can take place without the device needing moving parts. In this way the device is particularly reliable and of low maintenance.

In the following a further embodiment of the present invention is described on the basis of FIG. 9. Here a first and a second vessel 10, 20 are provided that are connected with one another through a connecting surface 11, 21 30. The connecting surface is in turn formed from the first side wall 11, the second side wall 21 and a bridging section 30. In addition heating elements 110 are provided on the connecting surface 11, 21, 30. The temperature of the magnetic particles can be increased by means of the heating elements so that, for example, drying the particles can be supported.

Cooling elements, for example Peltier elements, can also be provided on the connecting surface 11, 21, 30 in place of the heating elements in order to provide cooling of the magnetic particles and the materials adhering to the magnetic particles. In this way, for example, drying of the particles can be reduced should the analysis carried out require this.

Furthermore, the vessel 20 in the embodiment shown in FIG. 9 has additional functional elements 120, 130 which serve the preparation of subsequent analytical steps. At its base the vessel 20 has an outlet port 120 on whose interior a filter 130 is fitted.

Different aspects of the embodiment just described can naturally also be combined with the embodiments previously described. Thus, for example, individually controllable electromagnets can be arranged along a first side wall, a bridging section and a second side wall. Equally, a mechanical guide element, e.g. a drum or a rotary arm, could be directed along a connecting surface constructed separately as a separate bridge.

In all the embodiments described above the connecting surface could be constructed in the form of a groove. Furthermore, in all embodiments described the guide element could be so constructed that the rate with which the magnetic field(s) move along the connecting surface is controllable. In particular, the rate can be set to zero so that the pellet can be immobilised at its current position. Furthermore, in all embodiments described the guide element can be so constructed that the direction in which the magnetic field(s) move along the connecting surface is controllable. In particular, a direction reversal in the movements of the pellets is then possible. Furthermore, all the embodiments named above can be constructed as a closed system.

A still further embodiment of the present invention is represented schematically in FIG. 10. This is a so-called lab-in-a-chip in which a first and a second vessel 1010, 1020 are integrated into a cartridge 1000. The first and the second vessels 1010, 1020 are connected with one another by a bridging section 1030. The two vessels 1010, 1020 are constructed as chambers in the cartridge 1000 and filled with liquid. The second vessel 1020 could typically contain an elution filter. It is pointed out in this connection that FIG. 10 is merely a schematic representation in which the first and the second vessels are of equal size. Of course, the sizes of the individual vessels could deviate from one another. In particular, the volume of an elution vessel is typically smaller than that of a wash vessel.

A closure 1100 prevents the liquids mixing. However, the closure 1100 can be removed during the use of the cartridge. Optionally the closure 1100 is so constructed that after removal it can again be brought into the closed position and again act as a closure. The cartridge 1000 is typically provided with a lid in which there are two access openings 1012 and 1022. The access openings 1012, 1022 serve to introduce the magnetic particles into the vessels and to remove them again. The access openings 1012, 1022 can be provided with covers. Finally the cartridge has a magnet 1040 which can be directed along a wall of the first vessel 1010, the bridging section 1030 to a wall of the second vessel 1020 by a guide element 1050. In particular, the magnet 1040 can not only be directed along a side wall, but also along a cover plate, i.e. the lid or the base of the cartridge 1000.

Figure 11A:
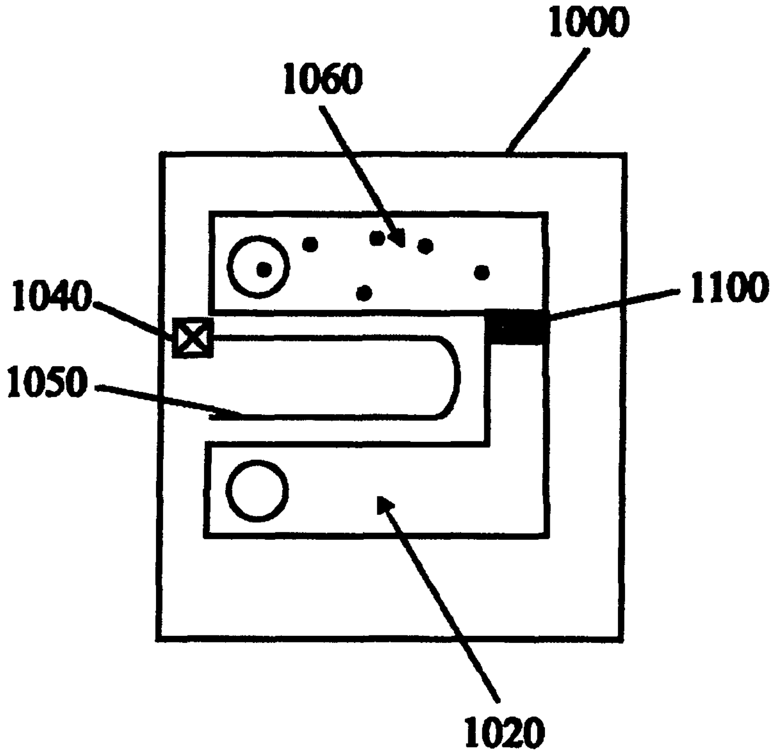
Figure 11B:
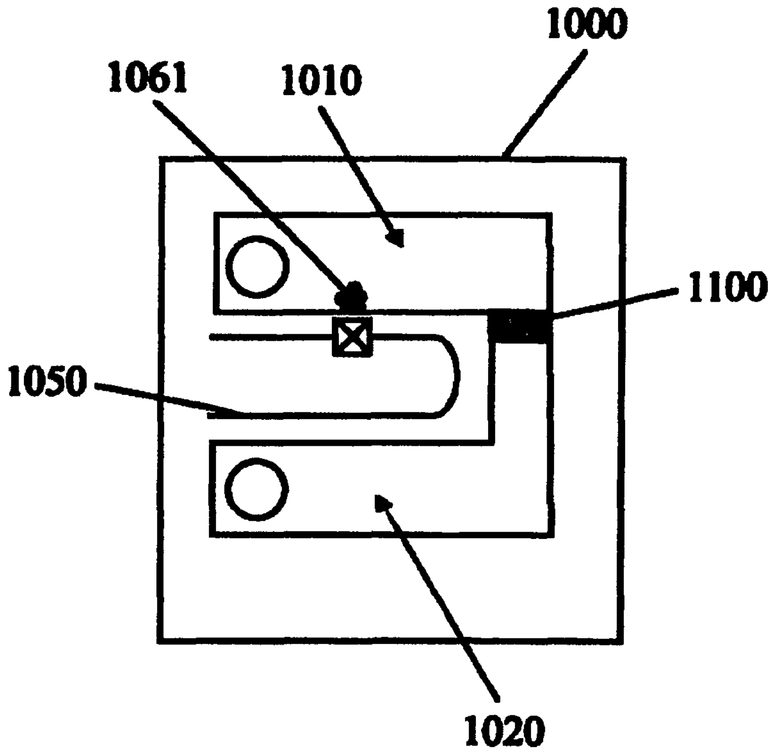
Figure 11C:
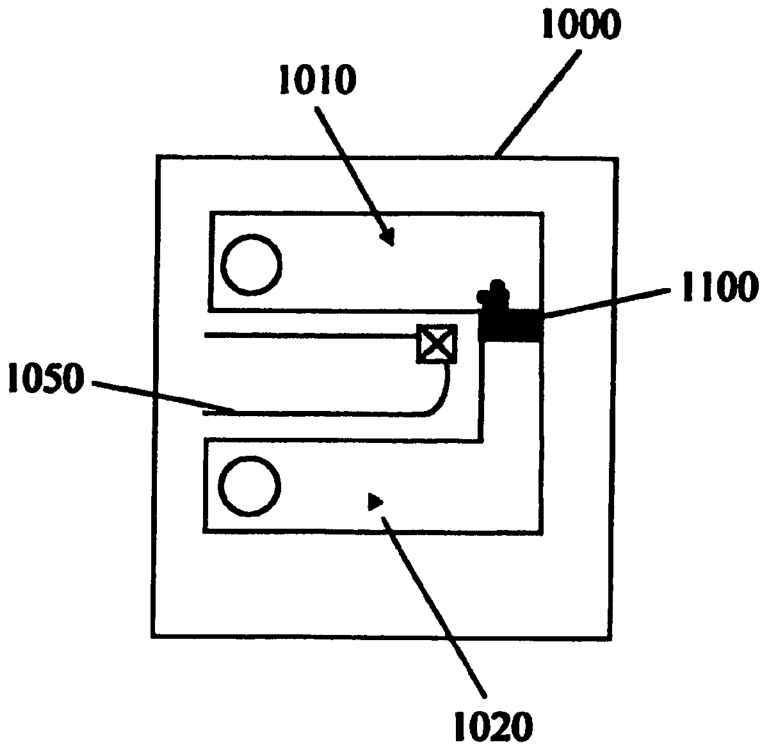
Figure 11D:
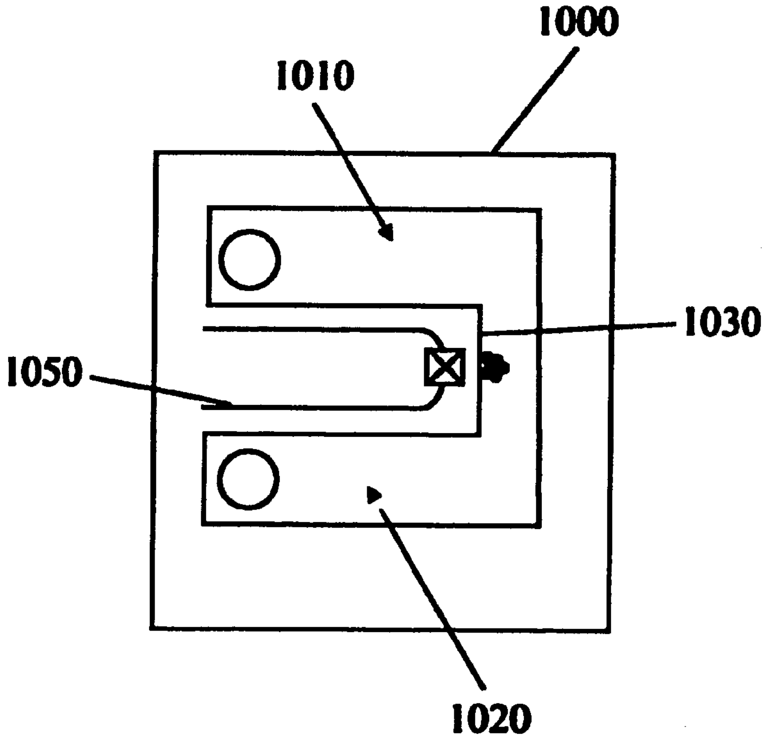
Figure 11E:
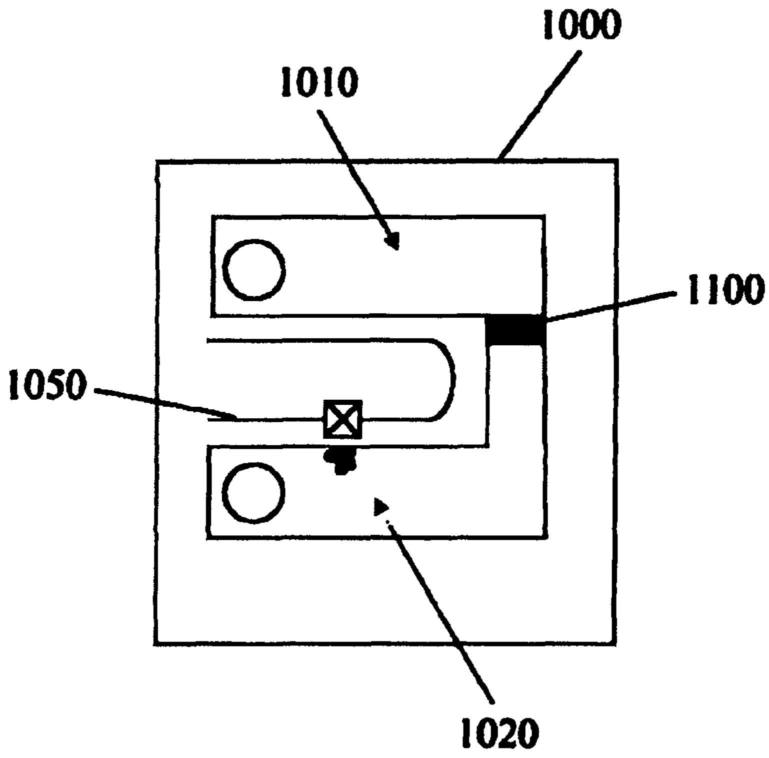
Figure 11F:
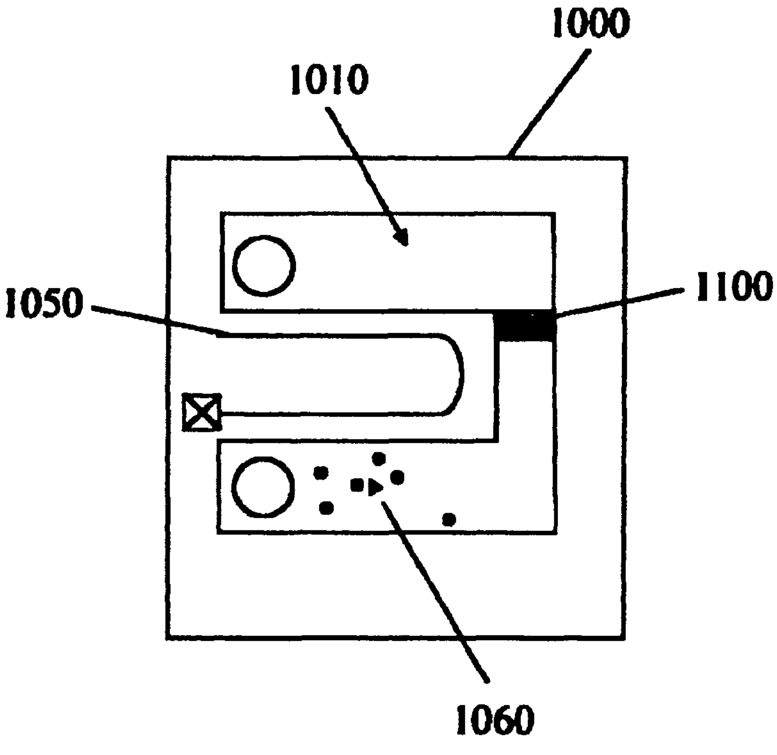

In the following the mode of operation of the embodiment of the present invention shown in FIG. 10 is described by means of the FIGS. 11A to 11F. As shown in FIG. 11A, the magnetic particles 1060 are introduced into the first vessel 1010 through the access opening 1012. If these particles 1060 are now to be removed from the liquid situated in the first vessel 1010 the magnet 1040 is placed into position with the guide element 1050. In this way a pellet 1061 is formed which is immobilised on the side wall of the first vessel 1010 (see FIG. 11B). The pellet 1061 is then directed to the closure 1100 (see FIG. 11C). The closure 1100 is now opened and the way for the pellet 1061 into the bridging section 1030 is freed (see FIG. 11D). Next the pellet 1061 is transported to the second vessel 1020 by the magnet 1040 (see FIG. 11E) where it then can be released (see FIG. 11F). If the magnetic particles 1060 are to be removed from the second vessel 1020 through the second access opening 1022 it is possible, using the magnet 1040, once more to form the magnetic particles 1060 into a compact pellet 1061 that can be easily removed through the opening 1022. It is equally possible to remove the liquid without the magnetic particles 1060 through the second access opening 1022. Typically, during the removal of the liquid the magnet 1040 would retain the pellet 1061 at a distance from the access opening 1022 so as to allow a removal of the liquid without accompanying magnetic particles.

A further embodiment of the present invention is shown in FIG. 12. Essentially the construction corresponds to the construction shown in FIG. 10, but a magnet arrangement similar to that shown in FIG. 8 is provided. Several electromagnets 1040 arranged continuously behind one another—from the first vessel 1010 to the second vessel 1020—are integrated into the cartridge 1000. For example, the cartridge 1000 could be constructed as an injection moulding component in which the electromagnets 1040 are embedded. The electromagnets are selected individually by a guide element 1050, i.e. in each case individually activated and deactivated. In this way a magnetic field running from the first vessel 1010 through the bridging section 1030 to the second vessel 1020 is produced. Pellet formation and the transport of the pellet from the first vessel 1010 to the second vessel 1020 then takes place similarly as in the embodiment shown in FIG. 8, for which reason a more precise explanation is omitted here.

FIG. 13 shows a perspective view of a further embodiment of the present invention. The interior of the cartridge 1000 shows here essentially the construction shown in FIG. 10. However, the magnet 1040 is located outside the cartridge 1000. With the help of the guide element 1050 it can be directed along the surface of the cartridge 1000 in such a way that under the influence of the magnetic force a pellet can move from the first vessel over the bridging section to the second vessel. In addition the magnet 1040 can be moved to and from the surface by the guide element 1050. In this way a pellet can be formed, for example, by lowering the magnet 1040 onto the surface of the cartridge above the first vessel. Equally the magnetic particles bound in a pellet can be released again in that the magnet 1040 is again raised from the surface of the cartridge.

A further embodiment of the following invention is shown in FIG. 14. Here the cartridge 1000 is arranged on a guide element 1050, which is constructed as a moveable carrier. The carrier 1050 is movable in its plane, but preferably also vertical to it so that the cartridge 1000 positioned on it can be moved over a predetermined path. A magnet 1040 is maintained essentially rigidly in position by a retainer 1045. By raising or lowering the carrier 1050 the surface of the cartridge 1000 can be brought into proximity of the magnet 1040. By moving the carrier 1050 in its plane the cartridge 1000 is moved under the magnet 1040 in a prescribable path. Fundamentally therefore the embodiment shown in FIG. 14 represents the reverse of the principle shown in FIG. 13.

FIG. 15 shows a development of the embodiment shown in FIG. 10. Here, in addition to the first and the second vessel 1010, 1020, a third vessel 1070 is located on the cartridge 1000. This third vessel 1070 is separated from the third vessel 1070 by a second closure 1200. In this way the second vessel 1020 could contain a wash solution and the third vessel 1070 an elution solution. It is to be understood that any number of additional vessels can be integrated on a cartridge and the exact number of vessels as well as the respective liquids contained therein are adapted to the respective application By means of the embodiments of the invention described above a separation of magnetic particles from a liquid is made possible which considerably reduces or even excludes the risk of cross-contamination. In particular, the devices according to the above embodiments of the present invention can be constructed and operated as closed systems. The devices and methods according to the embodiments of the present invention are simple and automation-compatible to a considerable extent.

The invention claimed is:

1. A device for the separation of magnetic particles from a liquid, the device comprising a first vessel having a first liquid and a first sidewall, a second vessel having a second liquid and a second sidewall, a connecting surface constructed in one piece and formed by the first sidewall of the first vessel, the second sidewall of the second vessel and a bridging section connecting the first and second sidewalls that runs from the interior of the first vessel to the interior of the second vessel, at least one first magnet for providing a magnetic field, and a first guide element for moving the first magnet along the first sidewall, along an underside of the bridging section and along the second sidewall of the connecting surface, wherein the first liquid and the second liquid are separate from one another.

2. The device according to claim 1, wherein the at least one first magnet is a permanent magnet.

3. The device according to claim 1, wherein the at least one first magnet is an electromagnet.

4. The device according to claim 1, wherein the first guide element is so constructed that the at least one first magnet is movable at a prescribed fixed distance from the side of the connecting surface.

5. The device according to claim 4, wherein the prescribed fixed distance is zero so that the magnet is in contact with the connecting surface as it moves along it.

6. The device according to claim 1, wherein the first guide element has at least one further magnet which is spatially separated from the first magnet.

7. The device according to claim 1, wherein at least one heating and/or cooling element is provided at the connecting surface.

8. The device according to claim 1, wherein the connecting surface is shaped as an arc.

9. The device according to claim 8, wherein the first guide element is so constructed that the at least one first magnet is movable on a circular path, wherein the radius (r) of the circular path is smaller than or equal to the radius (R) of the arc that is formed by the connecting surface.

10. The device according to claim 9, wherein the first guide element has at least one rotary arm whose one end is mounted on a rotating shaft and on whose other end the at least one first magnet is mounted.

11. The device according to claim 10, wherein the first guide element has one or more further rotary arms, wherein in each case one end is mounted on the rotating shaft and at least one further magnet is mounted at its respective other end.

12. The device according to claim 11, wherein the rotary arms are integrated.

13. The device according to claim 11, wherein the at least one first magnet and the at least one further magnet is in each case offset at a same angle to one another.

14. The device according to claim 9, wherein the first guide element takes the form of a cylinder that is mounted about a rotating shaft.

15. The device according to claim 14, wherein the at least one first magnet is mounted on a surface of the cylinder.

16. The device according to claim 14, wherein the at least one first magnet is in each case mounted within housings constructed in the cylinder.

17. The device according to claim 1, wherein the first guide element is so constructed that a speed at which it directs the at least one first magnet along the connecting surface is controllable.

18. The device according to claim 1, wherein the first guide element is so constructed that a direction in which it guides the at least one first magnet along the connecting surface is controllable.

19. The device according to claim 1, further comprising at least one third vessel that is connected with the first or the second vessel by means of a second connecting surface, and a second guide element to direct at least one further magnet.

20. The device according to claim 19, wherein the first guide element and the second guide element are attached to opposite sides of the second vessel.

21. The device according to claim 20, wherein the second liquid is a wash solution and the third vessel contains an elution solution.

22. The device according to claim 19, wherein the second liquid is a wash solution and the third vessel contains an elution solution.

23. The device according to claim 19, wherein the first vessel and the second vessel and/or the third vessel are arranged in a cartridge.

24. The device according to claim 23, wherein the first vessel, the second vessel and/or the third vessel are separated from one another by a removable closure.

25. The device according to claim 24, wherein the cartridge has a cover which has a first access opening to the first vessel and a second access opening to the second vessel.

26. The device according to claim 23, wherein the cartridge has a cover which has a first access opening to the first vessel and a second access opening to the second vessel.

27. The device according to claim 1, wherein at least one of the first and second vessels has a function element comprising an outlet and/or a filter.

28. The device according to claim 1, wherein the connecting surface is constructed in the form of a groove.

29. A method for the separation of magnetic particles from a liquid comprising:

(a) providing a first vessel having a first liquid and a first sidewall, a second vessel having a second liquid and a second sidewall, a connecting surface constructed in one piece and formed by the first sidewall of the first vessel, the second sidewall of the second vessel and a bridging section connecting the first and second sidewalls that runs from the interior of the first vessel to the interior of the second vessel, at least one first magnet for providing a magnetic field, and a first guide element for moving the at least one first magnet along the first sidewall, along an underside of the bridging section and along the second sidewall of the connecting surface, wherein the first liquid and the second liquid are separate from one another (b) providing a suspension of magnetic particles in the first liquid in the first vessel;

(c) producing at least one magnetic field at a first region of the connecting surface in an interior of the first vessel so that a pellet of magnetic particles forms at the first region;

(d) directing the at least one first magnet along the first sidewall, along an underside of the bridging section and along the second sidewall of the connecting surface, so that the pellet of magnetic particles is transported to an interior of the second vessel; and (e) removing the at least one magnetic field so that the magnetic particles forming the pellet are released.

30. The method according to claim 29, wherein at least a third vessel connected by a second connecting surface to the second vessel and a second guide element to direct at least one further magnet is provided, wherein the magnetic particles are washed in the second vessel after (e), and the magnetic particles are then transported from the second vessel into the third vessel by repeating (a) to (e) with the second guide element and the further magnet.

31. The method according to claim 30, wherein the washing magnetic particles in the second vessel comprises releasing the magnetic particles forming the pellet by removing the magnetic field by the first guide element, forming a second pellet by producing at least one further magnetic field through the second guide element, releasing the magnetic particles forming the second pellet by the at least one further magnetic field by the second guide element, and forming a third pellet by producing the magnetic field by the first guide element.

32. The method according to claim 31, wherein the producing the at least one magnetic field and the at least one further magnetic field is carried out by rotating the first or second guide element in a first rotation direction, whereby the first rotation direction of the first guide element is opposite to the first rotation direction of the second guide element, and wherein the removing the at least one magnetic field or the at least one further magnetic field is carried out by rotating the first or second guide element in a second rotation direction counter to the first rotation direction, wherein the second rotation direction of the first guide element is counter to the second rotation direction of the second guide element.

* * * * *